United States Patent [19]

Zison

[11] Patent Number: 5,063,519
[45] Date of Patent: Nov. 5, 1991

[54] LANDFILL GAS PRODUCTION TESTING AND EXTRACTION METHOD

[75] Inventor: Stanley W. Zison, Irvine, Calif.
[73] Assignee: Pacific Energy, Commerce, Calif.
[21] Appl. No.: 408,715
[22] Filed: Sep. 18, 1989
[51] Int. Cl.$^5$ .......................... G01N 7/14; E21B 43/22
[52] U.S. Cl. ................................... 364/510; 364/550; 364/558; 73/19.04; 73/19.05; 166/250
[58] Field of Search .................. 364/550, 551.01, 509, 364/510, 558; 73/19.04, 19.05, 154; 166/250, 251, 369

[56] References Cited

U.S. PATENT DOCUMENTS

| | | | |
|---|---|---|---|
| 4,026,355 | 5/1977 | Johnson et al. | 166/369 |
| 4,444,041 | 4/1984 | Zison | 73/19.04 |
| 4,487,054 | 12/1984 | Zison | 73/19.05 |
| 4,635,468 | 1/1987 | Hickam et al. | 73/19.04 |
| 4,777,383 | 10/1988 | Waller et al. | 364/510 |
| 4,866,633 | 9/1989 | Nakane et al. | 364/510 |
| 4,890,672 | 1/1990 | Hall | 73/154 |

OTHER PUBLICATIONS

"Methane Generation and Recovery From Landfills", by Emcon Associates, Ann Arbor, Mich., 1980 (pp. Title, v-vii, 15-18, 25-58, 65-95).
"State of the Art of Landfill Gas Recovery" by Emcon Associates, San Jose, Calif., 1981 (pp. 70-78).
"Landfill Methanogenesis: Literature Review and Critique", Halvadakis et al., Stanford, California, Aug. 1983.
"Ten Years of Landfill Gas Collection System Operation and Maintenance", Conrad et al., 1985.
"Landfill Gas Control at Metropolitan Toronto'Disco Transfer Station", Flewelling et al., 1986.
"Landfill Gas Horizontal Trench Collection System Keele Valley Landfill", Graziani et al., 1986.
"Gas Pressure and Concentration Gradients at the Top of a Landfill", Bogner et al., 1987.
"Understanding Landfill Gas Generation and Migration", Bogner et al., 1988.

*Primary Examiner*—Parshotam S. Lall
*Assistant Examiner*—Brian M. Mattson
*Attorney, Agent, or Firm*—Christie, Parker & Hale

[57] ABSTRACT

A method for determining total landfill gas production capability and pollutant emission rates involves measuring gas pressure in a soil cover at various locations around the landfill. These measurements are preferably made successively and repeated. The tester determines an average gas pressure and its spatial uncertainty envelope and measures soil pneumatic permeabilities by taking soil samples, preferably at various locations. The soil is tested to determine viscous and inertial resistance coefficients to characterize permeability. The gas composition is determined preferably at each pressure measuring location, and the coefficients, gas pressure and composition measurements are used to calculate total gas emission. A method of controlling gas extraction so that gas pressure in the soil cover approaches or becomes atmospheric pressure includes measuring gas pressure and relative permeability of the soil at various locations, relative flows of air into, or landfill gas out of, the surface are determined, and the extraction pressures at collection wells are adjusted in view of the flow through the soil until the relative flow at each location is zero or substantially zero.

24 Claims, 4 Drawing Sheets

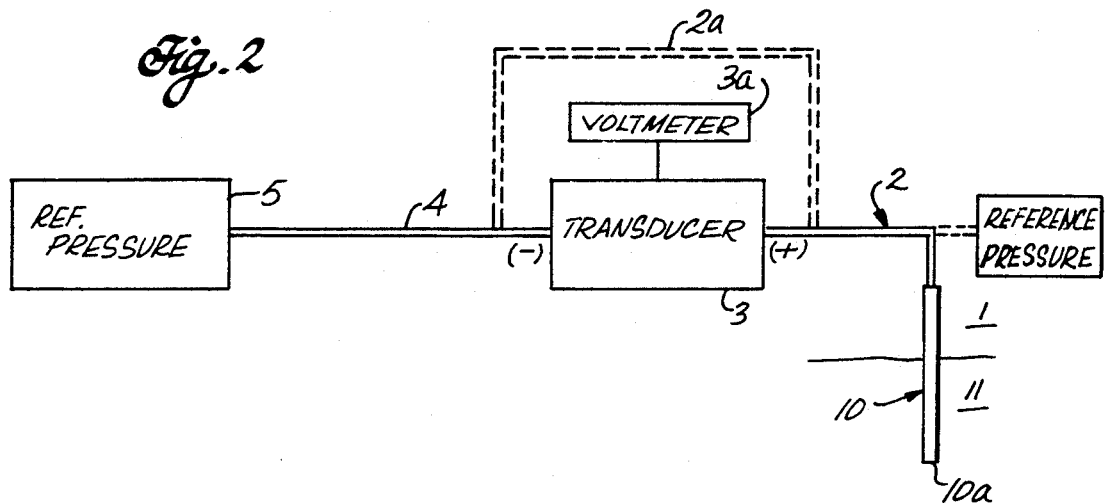
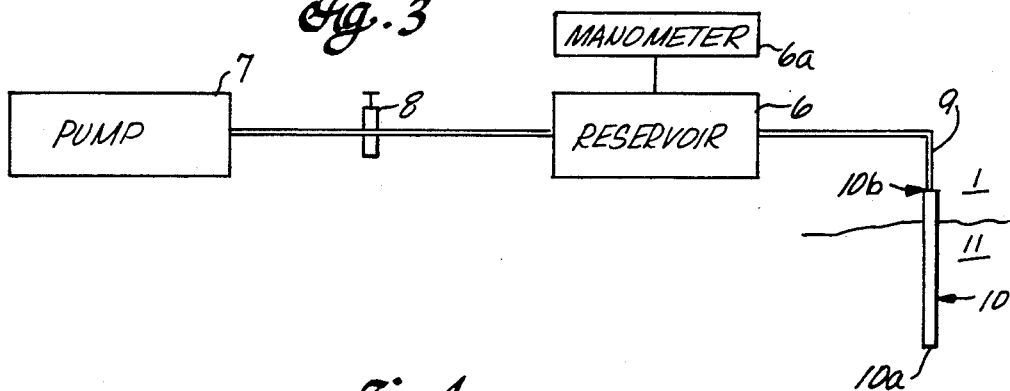
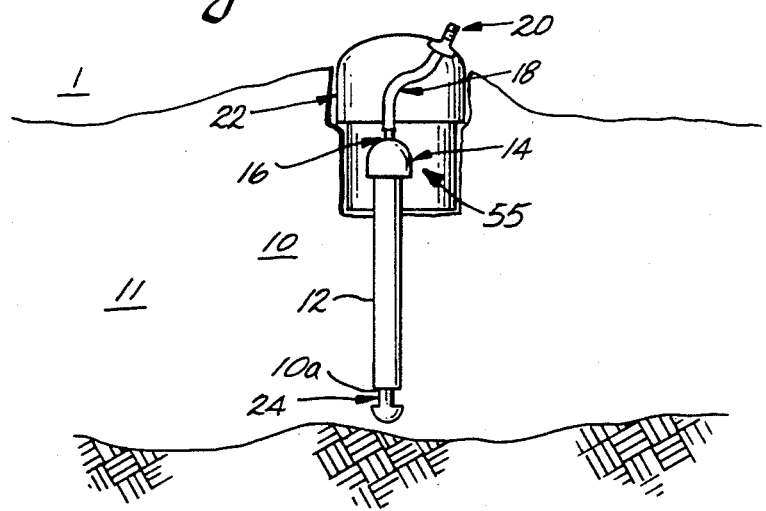

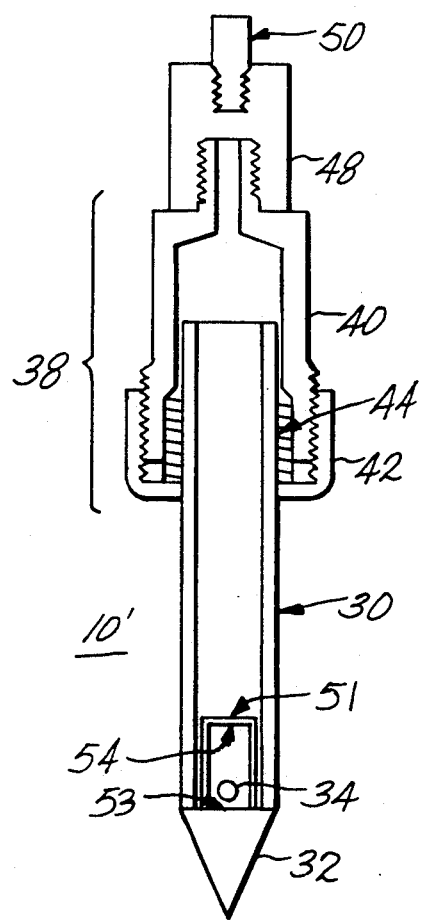

LANDFILL GAS PRODUCTION TESTING AND EXTRACTION METHOD

BACKGROUND OF THE INVENTION

This invention relates to a method for extracting gas emanating from a landfill. In particular, the invention relates to a method for determining the amount of gas emanating from the landfill and a method for optimizing collection of the gas.

Generally, a landfill is formed by depositing municipal solid waste and many other types of trash in a canyon or pit (or even on flat ground) and depositing soil on top of the trash. Usually, there are alternating layers of trash and soil, one atop another. The waste and soil layers are individually and collectively porous media through which gas may readily flow. The waste itself, including organic compounds such as cellulose, decomposes microbially. At first, this decomposition is aerobic and produces end products which are primarily carbon dioxide and water. After a while, usually ranging from a few weeks to several months, the waste consumes essentially all free oxygen and begins decomposing anaerobically. Then, microbes break down cellulose and other organic wastes and produce methane ($CH_4$) and carbon dioxide ($CO_2$) in substantially equal amounts. The methane gas is useful for fuel.

If free oxygen, such as in air, re-enters the waste, decomposition reverts to an aerobic process, and methane production ceases until essentially all of the free oxygen is again consumed. In general, and within limits, the longer the duration of aerobic decomposition, the longer the recovery time for methanogenesis (methane production). Introduction of air not only delays methanogenesis but also consumes trash that might otherwise have been converted to methane. Moreover, when nitrogen mixes with landfill gas, it is very difficult to purify the methane as may be required for some end uses. The normally occurring carbon dioxide can be removed efficiently, but processes required to remove nitrogen (e.g. cryogenics) are very costly. Air also creates a risk of underground fire and will exacerbate existing fires.

As anaerobic gas production continues, the methane concentration increases in the pores of the trash and soil, and the interstitial gas approaches the composition of the gas produced by the microbial cell itself. The mixture of methane and carbon dioxide (hereinafter "landfill gas" or "LFG") migrates within the landfill by diffusion (concentration-gradient driven mass transport) and advection (pressure-gradient driven mass transport). The LFG moves toward, and eventually saturates, soil and rock layers below and to the sides of the trash. The LFG also moves from the trash through the soil cover to the atmosphere. As the atmosphere is essentially an infinite sink for LFG, LFG keeps escaping along this latter route unless collected. As the gas pressure and LFG concentration increase in the surrounding soils, mass transport to those surrounding soils diminishes and after perhaps a few years, becomes negligible.

As methane is useful for fuel, optimal recovery is desirable. This makes proper collection system design and operation important. A perfect collection system is one which extracts all of the LFG but allows no air intrusion into the waste either by advective or diffusive mass transport. In the absence of an impermeable barrier between the waste and the atmosphere, this cannot be achieved. This is true since diffusion of air into the landfill readily occurs as the pressure regime immediately below the landfill-atmosphere interface approaches atmospheric pressure conditions. Without an impermeable liner, a perfect collection system, therefore, might be considered one which collects all of the LFG but which causes no advective air intrusion.

Common LFG collection systems consist of "wells" connected by pipes to a compressor or blower. Wells are normally vertically-oriented pipes installed in the trash (or in soil which is in pneumatic continuity with the trash). The pipes have perforations or slotted sections at the portions disposed in or near the trash. Alternatively, the wells are horizontal trenches or areas filled with gravel. These trenches or areas may be isolated from the atmosphere by a plastic liner or other impermeable barrier.

None of these common LFG collection systems meets either definition of a perfect collection system as they all admit some amount of air. Since this is the case, and in view of the various reasons for excluding air from the waste during the extraction process, a method is needed to optimally tune the collection system.

To collect LFG, the pressure in the well is reduced below that of the LFG in the landfill. The amount of "pull" exerted by the well on the LFG is controlled by operation of the compressor and/or by flow-controlling valves associated with the wells. Reducing the pressure too much will tend to pull air through the soil cover and into the landfill. However, the requisite amount of pull to cause air intrusion will vary with location of the well due to a variety of factors including unknown local LFG generation rates and the heterogeneities of the waste and soil in the landfill. That is, the LFG concentration, gas pressure, and pneumatic permeability of the porous medium around each well are unknown, spatially heterogeneous, and temporally variable. Therefore, it is difficult to extract all, or even most, of the LFG without locally introducing air into the waste.

The process of controlling flow into the wells is known as "tuning." There are relatively few techniques available for this process. One commonly used technique is to collect and chemically analyze one or more gas samples from the wells for relative concentrations of methane, carbon dioxide, nitrogen, and oxygen, or some combination of these gases. When methane concentration is relatively high and nitrogen is relatively low, for example, little or no air may be penetrating the landfill so the tuner increases the LFG extraction rate. When the gas is nitrogen rich and methane poor, when oxygen is in the gas, or when the molecular ratio of carbon dioxide to methane is high signalling substantial amounts of aerobic decomposition, the tuner reduces the extraction rate.

Even assuming that such chemical analysis correctly indicates whether to increase or decrease LFG flow into the well, there is no direct information on how much to increase or decrease flow. Generally, this process is hit-or-miss, especially since the composition of the landfill changes over time. Moreover, changes in LFG composition occur very slowly in response to changes in collection rates. In other words, if the collection rate is increased too much, i.e. sufficiently to introduce air, the resultant reduction in methane and increase in nitrogen in the well may not be detected for several weeks even though air begins to enter the landfill within minutes. If the extraction rate is too low, LFG escapes to the atmosphere, and based on well gas analysis alone, there is no way to tell how much additional gas can be collected by increasing the extraction rate without risking unacceptable atmospheric intrusion.

Another significant problem with LFG collection is determining whether or not the landfill produces sufficient LFG to justify building a gas collection and processing system. Moreover, where a collection system is in place, it is still possible that more gas could be collected if the collection system were to be upgraded. Determining the amount of gas produced can also aid in tuning the collection system, and negotiating energy sales contracts.

Commonly employed testing systems include using a full-scale collection system, a limited collection system with subsequent data extrapolation, waste decay kinetics modeling, laboratory waste decay studies, and tons-in-place estimates. A procedure based upon the cellulose-to-lignin ratio in the waste is sometimes used in conjunction with these other techniques.

Each of these methods suffers from significant drawbacks. For example, using a full-scale collection system is quite reliable but defeats the purpose of determining whether the collection system should be built in the first place. It also tends to be very costly. Where a limited collection system is used, the tester monitors flow rate and methane content of collected gas until they stabilize. This method necessitates extrapolation of the result to the entire landfill, which is very difficult and error-prone due to the heterogeneities of the waste and soil layers. One commonly used extrapolation method, known as the "radius of influence method," involves installing gas pressure monitoring probes radiating outward in one or more directions from a limited number of test wells installed for the purpose. The probes are at substantially the same depth as the slotted LFG intake sections of the wells. In one specific embodiment of this procedure, the tester measures pressures within the probes under non-extraction conditions and then under extraction conditions. In the process, the tester collects landfill gas pressure data from the probes. The tester also determines an extraction rate at which nitrogen begins appearing in the gas and the next lower incremental extraction rate at which there is no nitrogen (the "sustainable extraction rate" ). The pressure measurements so obtained are used to relate the difference in individual probe pressures under extraction and non-extraction conditions to the radial distances of the probes from the wells. The method assumes that at some distance from the well there will be no difference between the extraction and non-extraction probe pressures due to generation of LFG inside that distance sufficient to offset the extraction rate. This distance is taken to be the radius of a circle (the "radius of influence" ), which in turn, is said to define an "area of influence." The total rate of gas production in the landfill is given by the sustainable extraction rate multiplied by the ratio of total landfill area to the "area of influence." This method suffers from many drawbacks and appears to contradict physical laws such as conservation of mass. Because of significant heterogeneities in waste permeability, the approach appears to be unsatisfactory even as an approximation. It can yield total recoverable gas estimates that are incorrect by several orders of magnitude.

In the waste decay kinetics modeling method, the gas generation rate is estimated based on the history of waste disposed at the landfill. The laboratory waste decay study method usually involves taking samples of waste collected during drilling of the wells and attempting to maintain the samples under anaerobic conditions. At a laboratory, the cylinders are placed in a hot water bath and gas generation is monitored for a period of time. In the tons-in-place estimation method, the tester consults reference books or literature to obtain temporal gas yields per unit time and per unit volume or mass of waste in-place, and determines total gas yield based on an estimate of the total amount of waste in the landfill.

In the cellulose-to-lignin ratio method, the tester collects waste samples and determines a concentration of lignin and cellulose, the former being considered a cellulose-associated conservative species and the latter being the primary methane-producing substrate. Based upon concentrations of lignin and cellulose assumed for raw waste, the measured concentrations show what proportion of the original cellulose has decomposed. The tester estimates the total remaining cellulose in the landfill based on the non-decomposed proportions in the sample. The resulting data may be used, for example, to provide decay rate estimates for input to the waste decay kinetics modeling method.

Most, if not all, of these methods suffer from multiple and significant drawbacks including failure to take into account the heterogeneities of the landfill, the absence of proper statistical analysis for providing good confidence interval estimates of LFG production, suspect assumptions about flow and diffusion of gas in the landfill, and possible contradictions of fundamental and immutable physical laws.

In view of the above, there is a substantial need for a more accurate method of estimating LFG production, and a more accurate and faster method for tuning LFG collection systems.

SUMMARY OF THE INVENTION

The invention is a reliable, inexpensive, simple, quick and efficient tuning and testing method for landfill gas extraction. It is also a reliable, inexpensive, simple, quick, and efficient method for estimating rates of emission of landfill gas compounds into the atmosphere. As a major advantage, it recovers the greatest amount of methane from the landfill while allowing the landfill to produce methane at the greatest possible rate.

For energy recovery applications, the testing method assumes that the quantity of gas venting to the atmosphere is substantially the same as the amount of gas, or incremental amount of gas where LFG extraction is on-going, that may be collected. It is statistically based and provides not only an estimate of emitted or recoverable gas, but also the uncertainty envelope associated with that estimate.

In one form of the testing method, the tester measures gas pressures at some known depth in the soil cover at various randomly selected locations around the landfill. For best results, measuring occurs continually over a predetermined period of time such as a week or a month. For each probe, the tester determines a temporal average gas pressure for the time period of the test. The tester also collects a number of soil samples in the form of cylindrical cores which are of the same length as the probes. These samples can be continually collected over the time period of the test and are taken at random locations on the landfill surface which are independent of the probe locations. The tester uses the soil samples to determine representative soil pneumatic permeabilities. These permeabilities are expressed in terms of coefficients of viscous and inertial resistance to gas flow through the soil samples. From these coefficients and their spatial variability, the pressure data and their spatial variability and other data, the tester calculates the cumulative frequency distribution of LFG flow through the landfill surface. At selected times during testing, the gas coming from the probes is analyzed to determine its composition, and then, given flow and the gas composition (including its spatial variability), the total methane (or pollutant) production of the landfill is calculated along with its uncertainty envelope.

The tuning method maximizes LFG collection while minimizing entry of air into the landfill. In essence, the tuner monitors air flow into, and LFG flow out of, the landfill surface, and bases well valve settings and the LFG extraction rate on the rate and direction of the monitored surface flow. By monitoring flow at the soil interface with the atmosphere, the tuner adjusts the collection rate such that the pressure gradient at the interface is nearly zero everywhere, thereby eliminating flow of air into, and LFG out of, the landfill surface.

In one form, the tuner measures gas pressure at each of various locations around the landfill similar to testing, although measurements need not be taken over time. The tuner also measures the relative gas permeability of the soil around each probe. The tuner adjusts each measured gas pressure by dividing it by the measured relative permeability yielding an estimate of relative flow of air into, and LFG out of, the landfill-atmosphere interface. The tuner charts, plots, or otherwise determines the spatial relative flow distribution over the surface of the landfill by extrapolating from the measured pressures and permeabilities. The plot may take the form of a contour plot or a three-dimensional relief map. Based on areas of positive pressure (i.e. flow of LFG out of the landfill) and negative pressure (i.e. flow of air into the landfill), the tuner reduces the extraction rate of the wells near any negative pressure areas and increases the extraction rate near any positive pressure areas. The tuner's goal is to balance the pressure at all points on the landfill/atmosphere interface so that there is no net advective flow into or out of the soil. The process of measuring probe pressures and permeabilities, charting relative flows through the landfill surface, and adjusting well flow rates is repeated until each probe pressure indicates no net flow or is as close to that as possible.

This tuning method also can be used to provide estimates of supplemental gas available to collect although, unlike the testing method, it is not statistically based. Also, its use is restricted to where LFG is already being recovered. Given that LFG extraction is being carried out, the nitrogen content of that LFG is measured. Then, knowing the extraction flow rate and the extracted LFG nitrogen content, the absolute flow of air into the landfill can be computed. Assuming that nitrogen is conserved as it moves through the waste, this "calibrates" the volume under the relief surface representing atmospheric intrusion. The calibrated value obtained from air entering the landfill may be applied to LFG exiting the landfill and this yields an absolute estimate of additional gas available to collect.

The inventive testing and tuning methods are applicable not only to landfills, but also to other gas emitting surfaces such as superficial diatomaceous earth deposits that emit petroleum gas.

The above features and advantages of the invention as well as further features and advantages will become clearer upon reading the detailed description in conjunction with the drawings.

BRIEF DESCRIPTION OF THE DRAWINGS

FIG. 2 is a schematic of a device for testing gas pressure in the soil cover to carry out the inventive method;

FIG. 3 is a schematic of equipment for determining relative permeability of the soil in the vicinity of a gas pressure probe;

FIG. 4 is a cross-section of a probe suitable for use in the devices of FIGS. 2 and 3;

FIG. 5 is a cross-section of an alternative probe design suitable for use in the devices of FIGS. 2 and 3.

DETAILED DESCRIPTION OF THE INVENTION

The inventive LFG emission testing and extraction tuning methods both involve measuring the gas pressure and pneumatic permeability in the soil cover of the landfill proximate the soil and atmosphere interface.

LFG Testing Method

Figure 1:
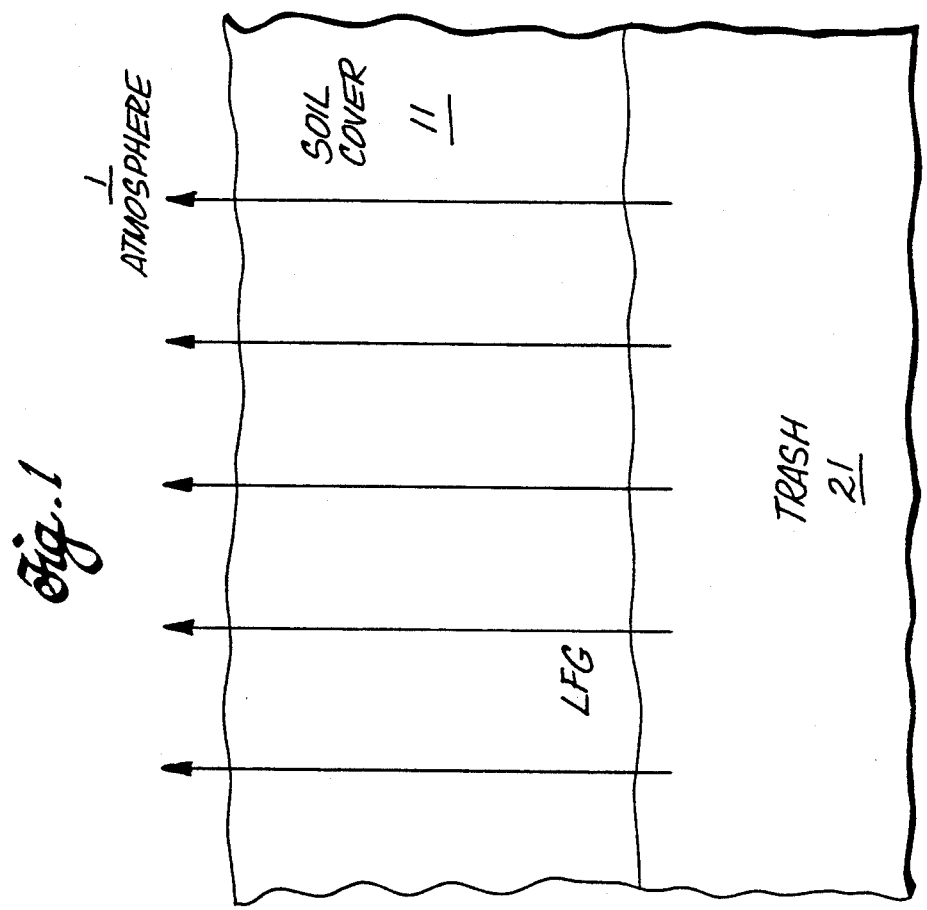
FIG. 1 is a diagram showing how gas generated in a landfill escapes to the atmosphere.

The LFG testing method determines how much LFG or LFG components flow to the atmosphere. That is, the method determines a total emission rate from soil cover 11 to atmosphere 1 of LFG or LFG components produced by trash 21 (FIG. 1).

The method is based upon equation (1) which relates one-dimensional, isothermal, steady flow of an ideal gas in a porous medium to the differential pressure in the direction of flow, the pneumatic permeability in the direction of flow, and several other variables and constants.

$$(p_1^2 - p_2^2)/L = 2ARTmG/Mg_c + [B + (1/L)\ln(p_1/p_2)][-2RTG^2/Mg_c]\ldots \quad (1)$$

where:
- $P_1$ = Absolute upstream pressure, lb force/ft$^2$ (gas pressure in probe or ambient pressure; $p_1 > p_2$)
- $p_2$ = Absolute downstream pressure, lb force/ft$^2$ (gas pressure in probe or ambient pressure; $p_1 > p_2$)
- L = Thickness of the medium (depth of probe), ft
- G = Superficial mass velocity of fluid, lb/sec ft$^2$
- m = Fluid dynamic viscosity, lb mass/ft sec
- $g_c$ = Gravitational constant, 32.17 ft lb mass/lb force sec$^2$
- M = Molecular weight (of the gas in the probes)
- R = Gas constant, 1546 ft lb force/lb mole deg R
- T = Absolute temperature, deg R
- A = Viscous resistance coefficient, 1/ft$^2$
- B = Inertial resistance coefficient, 1/ft See *Chemical Engineers' Handbook*, 5th ed., Perry, et. al. eds., McGraw Hill Book Co., N.Y., 1973. Page 5-54.

Solving equation (1) for G yields:

$$G = \{-(ARTm/Mg_c) + [(ARTm/Mg_c)^2 - (2RT/Mg_c)(B + \quad (2)$$
$$(1/L)\ln(p_1/p_2))((p_2^2 - p_1^2)/L)]^{.5}\}/(2RT/Mg_c)(B + (1/L)\ln(p_1/p_2))$$

Since several of the variables in equations (1) and (2) vary temporally and spatially during a landfill test, it is appropriate, although not requisite, that a statistical approach be taken to yield the uncertainty about G. The variables that should be considered random in these equations are A, B, p (at probe bottom only), m, M, and T. If a non-statistical approach is selected, the temporal and spatial averages for these variables may be used and G may be computed directly. However, such an approach defeats much of the benefit of the inventive method, that is, it lacks quantification of the uncertainties in the test results. If the statistical approach is taken, then G cannot be simply computed from equation (2). Instead, a cumulative frequency distribution for G must be developed.

There are several ways to approach such development. One is an analytical solution in which equation (2), or some modification of it, is further modified to introduce the cumulative frequency distribution expressions for the random variables. Explicit analytical solution for the probability distribution of G may be impracticable, however. A less difficult approach, and one which is useful regardless of the forms the observed data distributions may take is Monte Carlo simulation (see Rubinstein, Reuven Y., *Simulation and the Monte Carlo Method*, John Wiley & Sons, N.Y., 1981). Generically, Monte Carlo simulation represents the simulation of a probability experiment. With respect to the inventive method, it allows the tester to repeatedly simulate the by-then completed field test portion of the inventive method a very large number of times (e.g. a million times) while allowing the random variables to take on values prescribed by the observed data distributions obtained in the field. This is tantamount to re-running the field test that same number of times, computing G using averaged data each time (as just described in the non-statistical approach with a single computation of G) and observing the resulting cumulative frequency distribution of G. The goal is to obtain a distribution of G which is essentially the same as would have been obtained had a multitude of field tests actually been performed. The Monte Carlo approach will be discussed below to clarify the various steps involved.

To begin the overall test procedure, the tester initiates the field data collection process. First, the tester measures gas pressure in soil cover 11 proximate the interface with the atmosphere. The tester performs these measurements at various randomly selected locations around the landfill, preferably at a rate of between one and five per acre of landfill surface. The tester preferably makes pressure measurements over time at selected intervals, such as once every 15 minutes around the clock. Such frequent monitoring eliminates temporal uncertainty in the data (such as that due to barometric pressure and temperature changes), and greatly simplifies statistical analysis. The monitoring may be performed remotely by computer, and the entire data acquisition process may be remotely controlled and automated. It is also preferable that testing be conducted during a relatively stable period of weather.

A device suitable for performing the pressure measurements is shown in FIG. 2. The tester inserts a gas pressure probe 10, having a lower end with an opening 10a for gas inlet, to a depth in soil cover 11 sufficient to determine the pressure in the soil cover proximate the atmosphere. The exact depth of opening 10a is not critical, but for best results the opening should be as shallow as possible without getting too small a gas pressure reading in comparison with the accuracy (noise level) of the pressure measuring device. In addition, the tester should be careful to avoid inserting the probe into the trash or into a layer of soil with a significantly different permeability from the soil at the top of cover 11. In general, the depth of opening 10a is between about 1 and 5 feet. Examples of suitable gas pressure probes 10 for use in the testing method are shown in FIGS. 4 and 5 and will be described later.

A gas line 2 connects a valve at the top of probe 10 with the positive port of a gas pressure transducer 3. A line 4 connects a static pressure reference device 5 with the negative reference port of transducer 3. Transducer 3 converts gauge gas pressure to voltage, and a volt meter 3a displays the voltage. Prior to measuring probe pressure, the tester should zero and calibrate transducer 3. This is done by first connecting the positive and negative transducer ports together by means of line 2a and to reference device 5. The zero adjustment of transducer 3 is corrected to obtain a zero reading on volt meter 3a. Next, the positive transducer port is disconnected from reference device 5 by removing or otherwise blocking line 2a and is connected to a source of known pressure 10c at about a 3″ water column head, for example. The span adjustment of transducer 3 is adjusted to give the desired voltage reading on voltmeter 3a which will represent a 3″ water column head, for example. Suitable valves, not shown, may be used for these calibration purposes, and periodic zero monitoring and recording may be performed remotely by computer. The tester should use a transducer which is protected against wind effects, against large temperature changes, and against changes in its physical leveling.

To measure pressure, the tester disconnects line 2 from pressure source 10c, connects line 2 between probe 10 and the transducer positive port, and closes or disconnects line 2a. Pressure measurements are preferably made using a number of transducers, one dedicated to, and physically located at, each probe, i.e. the tester successively tests each probe and records the reading from transducer 3 and volt meter 3a in association with each probe. Alternatively, the tester remotely monitors the transducer located at each probe with the centrally located computer, the computer serving as the volt meter 3a and the data recording device. Regardless of whether the tester records data by visiting each probe or a computer is used for data acquisition, readings are continually taken over the predetermined time period at each selected interval.

In order to convert pressure to flow through the soil cover, it is necessary to characterize the pneumatic permeability of the cover [equations (1) and (2)]. As soil permeability varies quite a bit spatially, the spatial distribution of permeability is required. That is, permeability is considered a random variable in the inventive method. Provided the test is performed during a period of relative weather stability and lack of rain and sample acquisition is temporally randomized, temporal variability of soil pneumatic permeability may be neglected.

One way to determine soil permeability is to extract a sample, such as a cylindrical core of soil, and test its permeability by experimentation using well-known processes. For example, the tester puts one end of the core in an air reservoir, pumps air through the core and out to atmosphere, and measures the resulting flows, for two substantially different differential pressures. This testing yields gas permeability constants A and B, where A is the viscous resistance coefficient (e.g. in $ft^2$) and B is the inertial resistance coefficient (e.g. in $ft^1$).

Determination of A and B for any core sample may be made using a least-squares approach and developing the two necessary normal equations from equation (2). Alternatively, where only two flow settings are used experimentally as recommended here, a simpler iterative procedure may be employed. In this procedure, a value of A is arbitrarily selected and a trial B is calculated to satisfy one of the two experimental differential pressure/flow conditions. Next, using the trial A and B and the remaining differential pressure condition, the flow is calculated and compared with the experimental value. Since increasing one coefficient and decreasing the other while always satisfying one flow condition will monotonically move the solution toward or away from the other experimental flow condition, the direction of change necessary in A and B to satisfy both flow conditions quickly becomes clear and iteration to a solution is straight forward. This procedure is applied to all soil cores collected to provide the spatial distribution of coefficients A and B over the surface of the landfill.

The next aspect of field data collection is to characterize the gas escaping from the landfill surface, preferably by determining the composition of the gas present in the probes. This is necessary in order to obtain temporal mean values at each probe and spatial distributions over all probes for T, M, m, and gas methane (or pollutant) content. Gas composition may vary substantially over the test period. Accordingly, it may be necessary to frequently monitor gas quality in the probes over the test period to eliminate temporal uncertainty in the composition data.

T can be determined using a thermocouple probe installed at probe depth. Generally, it is not necessary to repeatedly measure T as G is not very sensitive to the small changes in T likely to occur at depth in the soil over a typical test period. T may also be found not to vary spatially to any significant degree, in which case it may be taken as a constant rather than a random variable. M and m are required by equation (2). They are readily computed from probe pressure, gas composition, and soil temperature data. The probe gas methane content is computed from the same data as used to compute m and M. The spatial distribution of methane content allows for conversion of the cumulative frequency distribution of G, the superficial mass velocity, to the cumulative frequency distribution for the rate of methane emission.

Specific ways to monitor temperature at probe depth, to determine gas composition (amount of $CH_4$, $CO_2$, etc.), and thus to determine T, methane (or pollutant) content, m and M, are evident to those of ordinary skill in the art.

Once the tester has collected all the field data, the tester computes the temporal average pressure for each probe. Since the pressure data have been collected very frequently at each probe, the temporal average at each probe is considered to be known with certainty. This is also true for gas composition even though composition data may be collected substantially less frequently than probe pressure. The tester computes the temporally averaged values for gas methane (or pollutant) content, m, and M for each probe, and may do so for T as well if T is considered a random variable. The tester computes values for resistance coefficients A and B for each soil core collected, based upon the experimental and computational procedures for the purpose described earlier.

Next, the tester examines the spatial data distributions for all variables to be considered random. The general form of the distributions are determined and the degree of statistical independence of each variable from each other variable is also examined. Methods to examine distributional forms and statistical independence are well documented in the statistical literature. Specifically, examining distributions may be accomplished by plotting frequency histograms. For example, if temporally averaged probe pressures spatially range from zero inches water column head to three inches water column head, the data might be divided up and the frequencies of pressures tabulated within the intervals 0–0.25, 0.25–0.50, ..., 2.75–3.0. If such data were to conform to a normal distribution, then the histogram would assume a bell-shape. If the data were to conform to an exponential distribution, then the histogram bars would be highest for low pressures to the left side of the histogram and would drop off at a decreasing rate moving toward the right. As alternative procedures, the data may be plotted on normal probability paper (which is readily available commercially) or the tester may apply the Kolmogorov-Smirnov (K-S) test or the chi-square goodness of fit test (see Ostle, Bernard, *Statistics in Research*, Iowa State University Press, Ames, Iowa, 1963, pages 126, 338, and 471).

Statistical independence is inherently more difficult to assess because of the many forms statistical dependence can assume. One approach to examining the data representing the random variables in equation (2) for statistical independence is to test for simple linear correlations. For example, the tester can correlate resistance coefficient A with B over the set of soil cores taken (using techniques that are well known to those with ordinary skill in the art and are described at Ostle, op. cit., pages 222–243). Typically, the coefficients are strongly correlated, A and B (or their simple mathematical transformation) representing samples from the bivariate normal distribution. Similarly, the methane (or pollutant) content of the probe gas is likely to be correlated to some degree with temporally averaged probe pressure since where the pressure is negative, air is drawn into the soil, and where the pressure is positive, LFG leaks past the probe and into the atmosphere.

Once the tester evaluates the random variables for distribution characteristics and the degree and nature of statistical interdependencies, the tester prepares to perform a Monte Carlo simulation.

Monte Carlo Considerations

There are many ways to develop Monte Carlo simulations, and the description provided here is but one example. In general, the tester must prepare a computer program to perform the simulation. The program may be written in FORTRAN, BASIC, or other appropriate computer language. These languages and methods of developing the necessary simulation program code are well known to those with ordinary skill in the art. The following comments all relate to the specific features required of the simulation program algorithm.

The random number generators needed for the simulation should be carefully tested to verify that they produce sufficiently long strings of independent and appropriately distributed random numbers. Generally, this can be accomplished by starting with a linear congruential random number generator; such generators are known to perform well, producing uniformly distributed random numbers in the interval (0, 1). From the output of such generator, sequences of independent random numbers conforming to other distributions can readily be obtained (see Yakowitz, S. J., *Computational Probability and Simulation*. Addison-Wesley Publishing Company, Inc., Reading, Mass., 1977).

The random number generators are to be used to repeatedly simulate the field test actually conducted exactly once. That is, they will be used to simulate, a great many times, the number of positive probes, the values for resistance coefficients A and B, the gas viscosity, m, the gas molecular weight, M, the gas methane (or pollutant) content, and the gas temperature, T, that might have been obtained were independent field tests to have been conducted that same great many times. Each such simulation yields one possible realization of the field test.

Once the tester has determined the types of random number generators to use to drive the Monte Carlo simulation, the next step in the program is to select a proportion of the landfill surface that is to be under positive pressure for the given realization. This is because the inventive method is concerned only with that portion of the landfill surface emitting LFG. The proportion that is under negative pressure has no bearing upon amounts of additional gas available to collect.

In general, in any landfill test, it can be expected that some number of probes may exhibit positive temporally averaged pressures. The remainder will exhibit zero or negative temporally averaged pressures. Accordingly, there will be some proportion, p, of positive probes and the remainder (1-p) can be called q, the proportion of probes that are not under positive pressure. Since the observed p and q are random samples and only approximately represent the true proportion of landfill surface that is under positive and non-positive pressure, respectively, these proportions may be considered to have been randomly drawn from an underlying binomial distribution. The probability of obtaining p and q is:

$$Prob(p,q) = \binom{n}{p}(P^p + Q^1)^n \cdots \quad (3)$$

where
- $\binom{n}{p}$ = The binomial coefficient
- P = The true proportion of the landfill surface under positive pressure
- Q = 1−P, the true proportion of the landfill surface not under positive pressure
- n = The number of probes monitored For example, if the true proportion of a landfill surface under positive pressure, P, is 0.8, and if ten probes have been monitored, the probability of obtaining four probes with positive temporally averaged pressure is:

$$Pi\ Prob(0.4, 0.6) = (210)(0.8^4)(0.2^6) = 0.005$$

As a second example, the probability of obtaining eight positive pressure probes of the ten monitored is:

$$Prob(0.8, 0.2) = (45)(0.8^8)(0.2^2) = 0.302$$

The outcome of the second example is obviously far more likely [Prob (0.8, 0.2)=0.302] than the first [Prob (0.4, 0.6)=0.0055].

For purposes of simulation in the inventive method, although the proportion of positive and non-positive pressures in the monitored probes do represent sampling from the (discrete) binomial distribution, the problem to be solved is not finding the probability of obtaining some proportion of positive probes given a known underlying proportion of the landfill surface that is under positive pressure. Rather, it is the inverse problem. That is, given some number of positive pressure probes, p, of n total probes monitored, the problem is to determine the (continuous) probability distribution for the (in fact unknown) proportion of the landfill surface that is under positive pressure. It is this distribution that must be simulated by Monte Carlo.

The specific approach to accomplish this will be addressed later. As an example, however, and simplifying by considering the possible proportions of the landfill surface under positive pressure to be in discrete steps of 0.1 so that there are exactly 11 possible states of nature (P=0.0, 0.1, 0.2, ..., 1.0), let p=0.6, q=0.4, and n=10. Further, let the a priori knowledge of the true state of nature be such that all 11 possibilities are equiprobable. Under these conditions, to find the probability, P, that the true proportion of the landfill surface under positive pressure is 0.7, compute:

$$Prob(P,Q) = Prob(p,q|P,Q) / \sum_{i=1}^{k} Prob(p,q|P_i,Q_i) \quad (4)$$

where
- Prob(P,Q) = The probability that the proportion of the landfill surface under positive pressure is P
- Prob(p,q|P,Q) = The probability of obtaining proportion, p, of positive probes given P,Q
- k = The number of possible proportions of the landfill that may be under positive pressure Specifically, $$Prob(p,q|P,Q) = Prob(0.6, 0.4|0.7, 0.3) = (210)(0.7^6)(0.3^4) = 0.2001$$

$$\sum_{i=1}^{k} Prob(p,q|P_i,Q_i) = (210)(.1^6)(.9^4) + \ldots + (210)(.9^6)(.1^4)$$

$$= .909$$

and, therefore, $$Prob(0.7, 0.3) = 0.2001/0.909 = 0.2201$$

Next, the tester develops computer program code to simulate the number of positive probes obtained for the realization, given the simulated proportion of the landfill that is under positive pressure. As part of this same step, the tester invokes the appropriate random number generator as suggested by the positive pressure cumulative frequency distribution developed from the field probe data. This distribution may tend to the exponential. That is, for example, $$Prob(p>x) = e^{-kx} \cdots \quad (5)$$

where:
- p = temporally averaged pressure in any probe installed in the positive pressure region of the landfill surface
- x = pressure (x ≥ 0)
- k = constant fitted to the data The fitted value of k may be obtained by least squares methods, graphically, or by other means well known to those having ordinary skill in the art. Alternatively, the positive tail of the normal distribution or the log normal distribution may prove most appropriate.

Next, the tester considers the field data distributions for the resistance coefficients A and B. In practice, A and B are not mutually independent and this must be taken into account in the simulation. Generally, the field data may be mathematically transformed (for example, by taking logs) so that transformed A and B represent sampling from the bivariate normal distribution (see *Encyclopedia of Statistical Sciences*, S. Kotz and N. J. Johnson eds., John Wiley & Sons, Inc., New York, 1982, pages 280-281). Accordingly, the tester constructs computer code to simulate sampling of A and B from the appropriate bivariate normal distribution. The tester also develops code to simulate sampling m, M, probe gas methane (or pollutant) content, and T if appropriate. Clearly, m, M, and probe gas methane (or pollutant) content are not mutually independent. Again, the tester takes the lack of independence into account in simulating realizations for these variables.

Finally, given the selected values for all the random variables required by equation (2), the tester constructs code to insert these values into that equation, yielding a realization for G (or rate of pollutant emissions, or recoverable methane as Btu's per unit time if desired). This is one realization of the objective of the simulation, which is subsequently repeated many times to yield the cumulative frequency distribution of G (or rate of pollutant emissions, or recoverable methane as Btu's per unit time if desired).

Monte Carlo Algorithm

A specific algorithm for a Monte Carlo embodiment in the inventive method might be as follows. In each case, "select" means "generate a random realization for," under the distribution constraints established through field data analysis.

1. Select the proportion of the landfill surface to be under positive pressure.
2. Given the proportion obtained in step 1, select the number of probes under positive pressure. If that number differs from the number obtained in the field, go to step 1. Otherwise, using the proportion obtained in step 1, select the number of probes to be taken as being under positive pressure. This procedure simulates the "inverse binomial sampling problem" to which reference was made earlier.
3. Select a positive pressure for each probe obtained in step 2. Examine the distribution parameters for the complete set of pressures obtained.
4. Using the distribution parameters obtained in step 3, select a positive pressure for each probe obtained in step 2. Examine the distribution parameters for these pressures, and if they are not within acceptable tolerance of the distribution parameters obtained from the field data, go to step 3. Otherwise, select yet a third set of positive pressures and compute the temporally and spatially averaged probe pressure to be entered into equation (2).
5. Using the same multi-step conditionally iterative procedure as in steps 1 and 2 and in steps 3 and 4, select A and B for a number of soil samples equal to the number taken in the field. Similarly select values for M, m, probe gas methane (or pollutant) content, and T, if appropriate.
6. Compute temporally and spatially averaged values for A, B, m, M, gas methane (or pollutant) content, and T.
7. Using the generated averages, compute spatially and temporally averaged G and, if desired, the spatially and temporally averaged recoverable methane or pollutant emission rate per unit area. Multiply both by the total area of the landfill under positive pressure to give total G (and/or methane) available to recover, or pollutant emitted per unit time. Store these values.
8. If the total number of realizations desired has not been processed, repeat steps 1-7. Otherwise, order the stored G and/or methane (or pollutant) content values and create a cumulative frequency distribution and histogram to approximate a cumulative probability function. The output is the estimated probability that the actual amount of LFG (or methane) available to collect (or pollutant emitted) exceeds each of the stored simulated values for total G, total methane, or total pollutant emitted.

The above method is applicable even where only a spatial distribution of temporally averaged probe gas pressure exists, and there are only average or representative amounts for the other variables in equation (2). However, for best results, at least a spatial distribution of temporally averaged gas composition and a spatial distribution of permeability are included.

If testing is performed in a landfill with an existing collection system, the test will determine the emitted amount of gas that could be collected if the system were more efficient. The total LFG production of the landfill is merely the collected LFG plus the LFG determined by testing.

Collection System Tuning

As described in the Background section, tuning involves setting extraction pressure (or a vacuum) on various collection wells to an amount intended to maximize LFG yield in terms of methane recovery per unit time without introducing air into the landfill. The inventive method tunes a collection system in such a way as to achieve atmospheric pressure conditions, or substantially atmospheric pressure conditions, in the top of the soil cover.

In the tuning system, as in testing, the tuner measures gas pressure near the top of soil cover 11 in FIG. 1. Probes that are used in testing are also suitable for use in tuning. The tuner places the probes in the same arrangement as in testing, or in areas where wells are located or some other distribution. In contrast to testing, the tuner obtains good results measuring pressure once at each probe in preparation for collection system tuning and just a few times at each probe during the tuning process, rather than multiple times a day over several days or weeks.

The tuner adjusts the probe pressure readings by taking into account permeability of the soil in the vicinity of the probe. One way to do this is to divide each probe pressure reading by a permeability measurement or factor. The tuner determines the permeability factor using the following process:

With reference to FIG. 3 and equation (6) (below), the tuner determines the value C, the rate of decline of vacuum for the test system open to the atmosphere. C characterizes the behavior of the test system itself and represents the value that would be obtained for pp of equation (7) (below) given a probe embedded in soil of infinite permeability. C may be in units such as seconds per inch of vacuum relieved. The tuner detaches line 9 from probe connector 10b and releases a clamp 8 to connect a vacuum pump 7 to a reservoir 6. The tuner turns on pump 7 to evacuate reservoir 6 to a selected amount, such as 55 inches of water column, above a first predetermined amount $V_1$, such as 40 inches, as measured on a manometer $6a$. The tester tightens clamp 8 and allows the pressure in reservoir 6 to freely drop to a second predetermined amount $V_2$, such as 20 inches. The time $t_c$ for this drop from $V_1$ to $V_2$ is measured, and the tuner calculates C using the following equation:

$$C = t_c/(v_1 - V_2) \ldots \quad (6)$$

After determining C, the tuner determines probe permeability pp by performing the same procedure as in determining C, except that line 9 is connected to probe 10 at probe connector $10b$. The following equation is used to determine pp, with $t_p$ representing the time to go from $V_3$, which for relatively small $t_p$ should be selected to be substantially the same as $V_1$, to $V_4$, which for relatively small $t_p$ should be selected to be substantially the same as $V_2$:

$$pp = t_p/(v_3 - V_4) \ldots \quad (7)$$

In practice, it may take quite a while for the vacuum to decline in the case where line 9 is connected to probe 10, so the tuner may need to make adjustments to $V_4$ accordingly. For example, if decline takes more than 60 seconds, $t_p$ could be taken as 60 seconds and $V_4$ would be the vacuum attained at 60 seconds.

The probe pressure is adjusted by dividing it by the value of pp−C. Since every probe must produce a value of pp>C, no undefined mathematical operation occurs. The relative flow at the tip of each probe, or the relative LFG emission rate or atmospheric intrusion rate in the vicinity of the probe, is given by the expression:

$$Q_4 = (P_m - P_z)/(pp - C) \ldots \quad (8)$$

where $P_m$ is measured pressure and $P_z$ is the transducer zero reading, both in units such as inches water column head. This net flow is not necessarily equal to the absolute amount of flow, and no units can properly be applied to $Q_r$ since the permeability of the probe pp and the correction factor (pp−C) are simply indexes. Nonetheless, the sign of $Q_r$ does indicate the direction of gas flow (negative indicates air into the landfill surface, and positive indicates LFG out of the surface), and one value of $Q_r$ can properly be compared with another. That is, a larger absolute value of Qr indicates a greater magnitude of flow than does a smaller absolute value of $Q_r$.

The object of tuning is to make the differential pressure between the interstitial gas at the top of the soil cover and the atmosphere zero for each probe. This is achieved when gas flow in the soil around probe opening $10a$ and normal to the landfill surface is zero.

Figure 6:
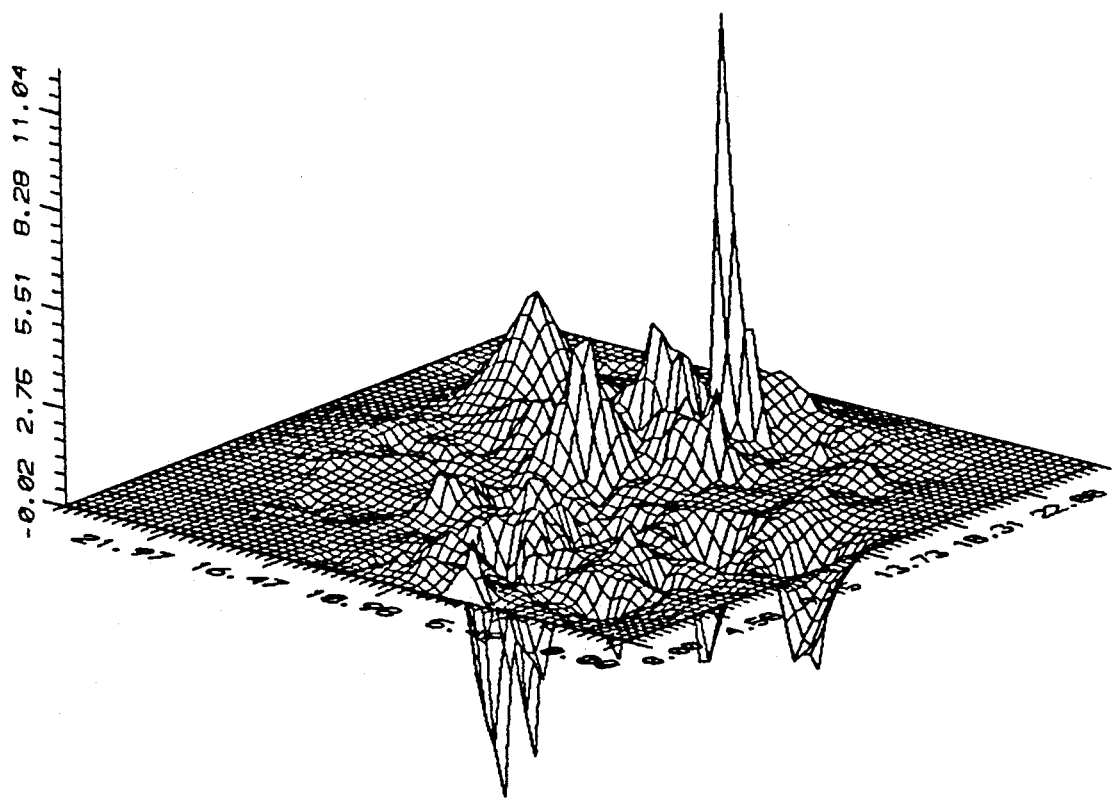
FIG. 6 is a sample 3-D plot of a landfill surface gas pressure distribution generated as part of the inventive tuning method.

Once the pressure readings are obtained, the tuner calculates and maps or charts the relative emission rates through the landfill surface. A plot may take the form of a two-dimensional contour plot or a three-dimensional relief map such as shown in FIG. 6.

Without actually plotting a map, the tuner may simply note which wells are near which probes, and change the vacuum applied to each well based on the $Q_r$ values obtained for the nearby probes. However, an actual plot of the distribution of flow across the landfill developed by Kriging, inverse square, or other reasonable contour surface estimation method is preferred. The tuner then superimposes the collection well locations on the plot and adjusts the well vacuum settings based on the pressures shown on the contour plot and resulting changes in probe readings near the well. Alternatively, the tuner adjusts the well vacuum setting while simply monitoring local probes, correcting the applied vacuum to make the probe pressure as near to atmospheric as possible. Since wells within some distance of one another interact, this becomes an iterative process of adjusting wells in sequence and repeating the process usually two to three times to obtain the best combination of settings which yields nearly atmospheric pressures in most or all of the nearby probes.

Although no algorithm has been developed to determine exactly how much to adjust the intake pressure from a given spatial distribution of relative emission rates and relative atmospheric intrusion rates, generally the tuner adjusts the intake pressure as follows:

(1) Increasing intake pressure where the relative flow at the corresponding surface location (the nearby probe or probes) is positive (LFG is emitted to the atmosphere), the more positive, the greater the increase; and (2) Decreasing intake pressure where the flow at the corresponding surface location (the nearby probe or probes) is negative (air is drawn into the landfill), the more negative, the greater the decrease. In both cases, the tuner monitors the nearby probe pressures and adjusts the well flow (well vacuum) to bring the probe pressure to zero or substantially to zero.

Even though each probe pressure in the landfill is affected by the extraction rate at each well in the landfill, the effect is significantly greater due to nearer wells. Generally, the further the probe from the well, the lesser the influence of well flow on probe pressure.

In practice, the probe pressure reacts quickly to well vacuum adjustments; generally the full impact is observed within about 15–30 minutes. After a first tuning, the tuner waits at least five to thirty minutes, remeasures the probe pressures, and readjusts the intake pressures as necessary based on the new probe pressures (i.e. new relative LFG emission rates or relative atmospheric intrusion rates). The tuner repeats this process until flow is zero or substantially zero or the judgement is made that, given the configuration of the collection system, no further improvement can be made.

Typically, tuning is conducted every one to two weeks. If greater extraction efficiency is desired, tuning is conducted more often, e.g. once every second day. For even more efficient extraction, one could remotely and continuously monitor probe pressure (and even permeability) and send the readings to a remote location where tuning is continuously carried out, e.g. by a computer which controls well flows based on the probe readings. Such a real-time servo-system embodiment of the invention is capable of substantially improving methane yields from landfills relative to manual tuning based on well gas quality or even manual tuning using the inventive method but without real-time collection system adjustment.

Probe Design

With reference to FIGS. 4 and 5, two alternative probe designs will be described although the inventive method does not rely upon any specific design. The only requirement for proper operation is that the probe have exactly two openings to the surroundings which will permit the advective flow of gas, one at the depth where soil interstitial gas pressures and soil permeabilities are to be measured, and one affording connection to the test equipment. In FIG. 4, probe 10 comprises a pipe 12 such as a galvanized iron pipe having a length of about one foot to about seven feet. Pipe 12 has a threaded top for receiving a threaded cap 14 made of PVC or the like. Top 14 has an aperture at which a hose barb 16 is connected. A vinyl tube 18 connects barb 16 to a sampling port 20, e.g. a positive seal compression fitting such as a Schrader valve. A slip cap 22 and short section of PVC pipe 55 houses and protects the components from the top of pipe 12 to valve 20. The bottom of pipe 12 has a carriage bolt 24 fitted therein to form a seal against the soil. To install probe 10, the tester (or tuner) excavates a small hole if necessary for slip cap 22 and pipe 55, and drives pipe 12 together with bolt 24 into soil 11 to a desired depth. Then, using a sufficiently long rod, the tester pushes or drives bolt 24 downward to create an opening 10a at the bottom of pipe 12. The tester threads cap 14 onto the top of pipe 12. The tester then connects hose barb 16 to valve 20 by means of flexible tubing 18, fits slip cap 22 and pipe 55 over the assembly and into the soil excavation, and backfills the hole with soil.

With reference to FIG. 5, a probe 10' is shown in which an iron pipe 30 has a hardened driving point 32 with a retaining pin 34. Bracket 51 is welded or otherwise fixed to hardened (conical-shaped) driving point 32 to form a point-bracket assembly, and this assembly is inserted in the end of pipe 30. Pin 34 fits into a hole in pipe 30 and passes through bracket 51. The pin 34 is firmly held in the hole in pipe 30 but allows movement of the point-bracket assembly longitudinally within pipe 30 from the position where driving point flat surface 53 contacts the bottom end of pipe 30 to where bracket surface 54 contacts pin 34. A probe top fitting 38 of PVC or similar material seals the top of pipe 30. Fitting 38 comprises a threaded fitting 40 with a threaded lower cover 42 for holding a rubber compression seal 44 in place. Fitting 38 has a threaded male upper end to receive coupling 48. Coupling 48 has a sampling port 50 threaded to its other end. Probe 10' is installed in a way similar to probe 10 to create an opening similar to opening 10a of FIG. 4.

Determination of Supplemental Gas Available

The tuning method also can be used to provide estimates of supplemental gas available to collect, although unlike the testing method, it is not statistically based. In addition, its use is restricted to where LFG is already being recovered. Given that LFG extraction is being carried out, the nitrogen content of that LFG is measured. Then, knowing the extraction flow rate and the extracted LFG nitrogen content, the absolute flow of air into the landfill is computed. Assuming that nitrogen is conserved as it moves through the waste, this "calibrates" the volume under the relief surface representing atmospheric intrusion. The calibrated value obtained from air entering the landfill may be applied to LFG exiting the landfill and this yields an absolute estimate of additional gas available to collect.

More specifically, where landfill gas is extracted for energy recovery or other purposes, the gas is routinely analyzed for its methane, carbon dioxide, nitrogen, and oxygen content. Since virtually all of the nitrogen in the gas originates in the air pulled into the landfill due to excessively high local LFG extraction rates, and assuming the nitrogen is not significantly reduced as the air travels through the waste, then the nitrogen content of the extracted gas and the gas flow may be used to compute the amount of air pulled into the landfill. For example, if the gas flow is 1 million cubic feet per day and the nitrogen content is 10 percent, then 100,000 cubic feet per day of nitrogen is being pulled into the landfill. Since air is approximately 78% nitrogen, the amount of air pulled into the landfill is 100,000/0.78=128,205 cubic feet per day or 89 cubic feet per minute.

The inventive tuning method includes the application of the Kriging algorithm or inverse square algorithm for generating a three-dimensional relief map of the positive relative flow (LFG emitting) areas and the negative relative flow (air intrusion) areas of the landfill. Generally, the computer contouring algorithm uses a regular x, y Cartesian coordinate grid system with the x and y axes representing the east-west and north-south directions on the landfill surface. Each grid location is assigned a computed value (on the z axis) corresponding to relative flow. The resulting map (see FIG. 6) constitutes a three-dimensional contour surface with the positive region collectively defining some volume above the zero relative flow plane, and, correspondingly, the negative regions collectively defining some volume below the zero plane. Since the negative volume region represents atmospheric intrusion, the known air intrusion rate may be used to calibrate the negative relative flow volume and convert it to absolute flow. The positive relative flow volume is then compared with the absolute negative flow volume to estimate the absolute amount of LFG emitted to the atmosphere.

For example, if the tuning process involves 100 probes with relative flow measured at each, and the contouring algorithm is set to generate a 60 by 60 grid, the grid will contain $60 \times 60 = 3600$ relative flow values estimated from the 100 observations. Some portion of the grid will exhibit negative relative flows. Since the grid elements are uniform in size, each of the 3600 elemental areas can be taken to represent unit area and the volume under the relative flow relief surface for each elemental grid area is simply the value of the relative flow itself for that area. The sum of the positive relative flows is, therefore, the total volume between the positive region of the contour surface and the zero relative flow plane. Similarly, the volume between the negative relative flow surface and the zero relative flow plane may be calculated. The volume of the negative relative flow region represents the volumetric flow of air intruding into the waste. Continuing the example, let the positive relative flow volume be 3204 and the negative relative flow region be 356 units. The value for the negative region divided by the known air intrusion rate calibrates the elemental volume of the contour plot. That is, 356 volume elements/89 cubic feet per minute=4 volume elements per cubic foot per minute or 0.25 cubic feet per minute per volume element. Then the amount of LFG escaping (and potentially available to collect) is $0.25 \times 3204 = 801$ cubic feet per minute.

What is claimed is:

1. A method of determining flow of a gas component through a surface of ground, the method comprising the steps of:
    measuring a gas pressure at a selected depth below the surface multiple times at each of a first plurality of locations with respect to the surface over a predetermined period to obtain a temporal average gas pressure for the predetermined period at each of the first plurality of locations and a spatial distribution of the average gas pressure;

determining pneumatic permeability of the ground at a second plurality of locations with respect to the surface to obtain a spatial distribution of permeability;

measuring a gas component at a third plurality of locations to obtain a spatial distribution thereof; and determining gas component flow through the surface based on the temporal average gas pressures and their spatial distribution and the spatial distributions of permeability and gas component.

2. The method of claim 1, wherein a cumulative distribution of gas component flow is determined.

3. The method of claim 2, wherein the cumulative distribution is determined using Monte Carlo simulation.

4. The method of claim 1, wherein the gas component is methane emanating from a landfill.

5. The method of claim 1, wherein a temporal average permeability for the predetermined period is determined for each of the second plurality of locations, and the determination of gas component flow is also based on the temporal average permeability.

6. The method of claim 5, wherein a cumulative distribution of gas component flow is determined.

7. The method of claim 1, wherein the determination of gas component flow is also based on the selected depth, gravitational constant, molecular weight of the gas, gas constant, temperature of the gas, and fluid dynamic viscosity of the gas.

8. The method of claim 1, wherein each location of the first plurality and third plurality of locations is selected randomly.

9. The method of claim 1, wherein each location in the third plurality of locations coincides with a location in the first plurality of locations.

10. The method of claim 1, wherein the gas component emanates from a landfill having a cover layer comprising soil, and wherein there are from one to five locations, for measuring gas pressure, per acre of the surface of the landfill, the selected depth is from one to five feet, the permeability is measured to the selected depth, the predetermined period is at least a week, and the pressure is measured about every fifteen minutes.

11. The method of claim 1, wherein the gas is generated underground, and a generation rate of the gas is determined by equating the generation rate to the gas component flow through the surface.

12. The method of claim 1, wherein the gas is generated underground, and at least part of the gas is collected and wherein the method further comprises the steps of determining a rate of collection of the gas and determining a generation rate of the gas by combining the gas component flow through the surface with the collection rate.

13. A method of controlling an extraction rate of gas from ground at various positions in the ground at which the gas is extracted, the method comprising the steps of:

determining gas pressure below a surface of the ground at multiple locations with respect to the surface;

determining a relative permeability of the ground to the gas at each of the locations;

calculating an adjusted value of the gas pressure at each of the multiple locations based on the relative permeability; and adjusting the extraction rate at each of the positions in the ground at which the gas is extracted based on relative flow of the gas into and out of the ground as indicated by the adjusted values of the gas pressure.

14. The method according to claim 13, wherein the ground comprises a landfill comprising trash and a soil cover, and the gas pressure is determined in the soil cover.

15. The method according to claim 13, wherein the gas pressure is determined relative to atmospheric pressure, the adjusted value of gas pressure is calculated by dividing by the relative permeability at each of the locations to yield the adjusted gas pressures, the adjusted gas pressures are used to determine a relative flow distribution with respect to the surface of the ground, and the extraction rate at each one of the positions is adjusted based on a value of the relative flow distribution corresponding to the one of the positions.

16. The method according to claim 15, wherein the relative flow distribution is a spatial relative flow distribution obtained by at least one of Kriging and inverse square calculations.

17. The method according to claim 15, wherein the extraction rate is increased at positions where the relative flow is positive and decreased at positions where the relative flow is negative, where positive indicates flow out of the ground and negative indicates flow into the ground.

18. The method according to claim 15, wherein after adjusting the extraction rate, the steps of determining relative gas pressure and relative permeability and the steps of adjusting the gas pressure and the extraction rate are repeated until the relative gas flow is zero over the surface of the ground.

19. A method of controlling an extraction rate of gas from underground positions in a landfill comprising trash and a cover layer, the method comprising the steps of:

determining gas pressure relative to a reference pressure at a predetermined depth in the cover layer at multiple locations with respect to a surface of the landfill;

determining permeability of the cover layer to the predetermined depth at each of the multiple locations relative to a reference amount;

dividing each gas pressure by each relative permeability, respectively, to obtain a relative flow;

obtaining a spatial distribution of the relative flow; and increasing the extraction rate at positions corresponding to positive flow and decreasing the extraction rate at positions corresponding to negative flow, where positive flow represents gas flow out of the landfill and negative flow represents air flow into the landfill.

20. The method of claim 19, wherein the greater the positive flow the greater the increase in extraction rate, and the greater the negative flow the greater the decrease in extraction rate.

21. The method of claim 19, wherein the method is repeated until the flow is zero over the surface of the landfill.

22. The method of claim 19, wherein relative permeability is determined by measuring a rate of decline of a vacuum open at the predetermined depth, and subtracting therefrom a rate of decline of a vacuum open to atmosphere.

23. A method of extracting gas from various underground positions and determining an additional amount of gas that can be extracted from the underground, the method comprising the steps of:

extracting the gas;

determining gas pressure relative to a reference pressure at a predetermined depth underground at multiple locations with respect to a surface of the ground;

determining permeability of the ground to the predetermined depth at each of the multiple locations relative to a reference amount;

dividing each gas pressure by each relative permeability, respectively, to obtain a relative flow having areas of negative relative flow and positive relative flow;

obtaining a spatial distribution of the relative flow; and determining an amount of additional gas that can be extracted by summing up relative positive flow amounts to obtain a total positive relative flow and multiplying the positive relative flow by a calibration factor, the calibration factor being obtained by determining a total flow rate of air into the ground, summing up the negative relative flow rate to obtain a total negative relative flow, and taking a ratio of the total flow rate of air and the total negative relative flow.

24. The method of claim 23, wherein the total flow rate of air is determined by measuring a nitrogen content of the gas extracted from the ground, and an extraction rate of the gas, multiplying the nitrogen content of the gas and the extraction rate, and dividing by a percentage of nitrogen content of air.

* * * * *

UNITED STATES PATENT AND TRADEMARK OFFICE
CERTIFICATE OF CORRECTION

PATENT NO. : 5,063,519

DATED : November 5, 1991

INVENTOR(S) : Stanley W. Zison

It is certified that error appears in the above-identified patent and that said Letters Patent is hereby corrected as shown below:

Column 3, line 56, change "$($the "radius of influence" $),$" to -- (the "radius of influence"), --.

Column 6, line 44, change "]B+" to -- [B+ --.

Column 11, line 41, change "$Q^1$" to -- $Q^q$ --.
Column 11, line 55, before "Prob" delete "Pi".
Column 11, line 55, change "0.005" to -- 0.0055 --.

Column 15, line 7, change "$t_c$for" to -- $t_c$ for --.
Column 15, line 26, change "kaccordingly" to -- accordingly --.
Column 15, line 36, change "$Q_4$" to -- $Q_r$ --.

Signed and Sealed this

Sixth Day of April, 1993

*Attest:*

STEPHEN G. KUNIN

*Attesting Officer*   Acting Commissioner of Patents and Trademarks